(12) United States Patent
Holt

(10) Patent No.: US 10,675,175 B2
(45) Date of Patent: Jun. 9, 2020

(54) MALE CATHETER

(71) Applicant: Katelyn Patricia Holt, Warwick, RI (US)

(72) Inventor: Katelyn Patricia Holt, Warwick, RI (US)

(73) Assignee: Katelyn P. Holt, Warwick, RI (US)

( * ) Notice: Subject to any disclaimer, the term of this patent is extended or adjusted under 35 U.S.C. 154(b) by 502 days.

(21) Appl. No.: 15/620,156

(22) Filed: Jun. 12, 2017

(65) Prior Publication Data

US 2017/0354532 A1   Dec. 14, 2017

Related U.S. Application Data

(60) Provisional application No. 62/349,306, filed on Jun. 13, 2016.

(51) Int. Cl.
*A61F 5/453* (2006.01)
*A61F 5/44* (2006.01)

(52) U.S. Cl.
CPC ............ *A61F 5/453* (2013.01); *A61F 5/4408* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,789,560 A * | 4/1957 | Weimer | ................... | A61F 5/453 604/349 |
| 3,339,551 A * | 9/1967 | Stoutenburgh | ........ | A61M 39/12 604/349 |
| 3,394,703 A * | 7/1968 | Orgel | ...................... | A61F 5/453 604/353 |
| 3,511,241 A * | 5/1970 | Lee | ......................... | A61F 5/453 604/352 |
| 3,608,552 A * | 9/1971 | Broerman | ............... | A61F 5/453 604/349 |
| 3,631,857 A * | 1/1972 | Maddison | ............... | A61F 5/453 604/349 |
| 3,661,156 A * | 5/1972 | McLaughlin | .......... | A61F 5/453 604/349 |
| 3,739,783 A * | 6/1973 | Broerman | ............... | A61F 5/453 604/349 |
| 3,835,857 A * | 9/1974 | Rogers, III | ............ | A61F 5/453 604/349 |
| 3,998,228 A * | 12/1976 | Poidomani | ............. | A61F 5/453 604/351 |
| 4,284,079 A * | 8/1981 | Adair | ...................... | A61F 5/453 600/573 |
| 4,475,909 A * | 10/1984 | Eisenberg | ............... | A61F 5/453 600/573 |

(Continued)

FOREIGN PATENT DOCUMENTS

EP        2008624 A1      12/2008

*Primary Examiner* — Tatyana Zalukaeva
*Assistant Examiner* — Guy K Townsend

(57) ABSTRACT

Apparatus and methods for a male catheter. An assembly includes a proximal region including a sheath portion, the sheath portion including a braided section terminating in a proximal region opening adapted to encompass a male penis, a distal region including a connection portion, the connection portion terminating in a distal region opening to enable linking to one or more external devices, and a tube portion linking the proximal region to the distal region.

14 Claims, 3 Drawing Sheets

(56) References Cited

U.S. PATENT DOCUMENTS

| | | | | |
|---|---|---|---|---|
| 4,475,910 A * | 10/1984 | Conway | A61F 5/453 | 604/349 |
| 4,540,409 A * | 9/1985 | Nystrom | A61F 5/453 | 206/229 |
| 4,553,968 A * | 11/1985 | Komis | A61F 5/453 | 604/349 |
| 4,588,397 A * | 5/1986 | Giacalone | A61F 5/453 | 604/349 |
| 4,713,066 A * | 12/1987 | Komis | A61F 5/453 | 604/349 |
| 4,738,673 A * | 4/1988 | Shepard | A61F 6/04 | 604/327 |
| 4,759,753 A * | 7/1988 | Schneider | A61F 5/453 | 604/352 |
| 4,769,020 A * | 9/1988 | Eaton | A61F 5/453 | 604/352 |
| 4,846,816 A * | 7/1989 | Manfredi | A61F 5/4405 | 604/323 |
| 4,932,948 A * | 6/1990 | Kernes | A61F 5/453 | 128/844 |
| 4,957,487 A * | 9/1990 | Gerow | A61F 5/44 | 604/133 |
| 5,009,649 A * | 4/1991 | Goulter | A61F 5/453 | 604/349 |
| 5,336,211 A * | 8/1994 | Metz | A61F 5/453 | 604/352 |
| 5,423,784 A * | 6/1995 | Metz | A61F 5/453 | 604/351 |
| 5,531,725 A * | 7/1996 | Steer | A61F 5/453 | 128/844 |
| 5,797,890 A * | 8/1998 | Goulter | A61F 5/453 | 604/351 |
| 6,007,526 A * | 12/1999 | Passalaqua | A61F 5/453 | 128/844 |
| 6,113,582 A * | 9/2000 | Dwork | A61F 5/453 | 604/349 |
| 6,117,120 A * | 9/2000 | Heininger | A61F 5/453 | 604/347 |
| 6,551,293 B1 * | 4/2003 | Mitchell | A61F 5/453 | 604/327 |
| 6,632,204 B2 | 10/2003 | Guldfeldt et al. | | |
| 7,018,367 B2 * | 3/2006 | Nava | A61F 5/453 | 4/144.3 |
| 7,077,833 B2 * | 7/2006 | Bonham | A61F 5/44 | 604/323 |
| 7,186,245 B1 * | 3/2007 | Cheng | A61F 5/44 | 604/349 |
| 8,353,886 B2 * | 1/2013 | Bester, Jr. | A61F 5/453 | 604/327 |
| 2002/0026163 A1 * | 2/2002 | Grundke | A61F 5/453 | 604/347 |
| 2005/0075615 A1 * | 4/2005 | Bonham | A61F 5/44 | 604/327 |
| 2007/0142794 A1 * | 6/2007 | Bester, Jr. | A61F 15/002 | 604/349 |
| 2008/0183157 A1 * | 7/2008 | Walters | A61F 5/453 | 604/544 |
| 2011/0054428 A1 * | 3/2011 | Hill | A61F 5/453 | 604/349 |
| 2015/0045757 A1 * | 2/2015 | Lee | A61F 5/4401 | 604/385.03 |
| 2015/0209647 A1 * | 7/2015 | MacFarland | A41D 13/0506 | 2/466 |
| 2017/0354532 A1 * | 12/2017 | Holt | A61F 5/4408 | |

* cited by examiner

MALE CATHETER

CROSS REFERENCE TO RELATED APPLICATIONS

This application claims priority under 35 USC § 119(e) to U.S. Provisional Application Ser. No. 62/349,306, filed on Jun. 13, 2016, and entitled MALE CATHETER, the entire contents of which are hereby incorporated by reference.

BACKGROUND OF THE INVENTION

The present invention relates generally to medical catheters, and more particularly to an external male catheter.

At various times, men can become incontinent or bed-ridden. In such circumstances, it is desirable to collect the urine in a container for subsequent disposal rather than to wear a bulky diaper. Most commonly, a "Texas" condom catheter is used. The Texas catheter includes a condom-like sheath made of silicone rubber or latex. The sheath envelops the penis like a condom but forms a distal opening that can be connected to a hard rubber tube to a drainage bag. An adhesive glue is built into the condom to keep the condom in place, but with the slightest movement or weight of the drainage bag, the condom may come off.

During urination, the urine passes through the drainage tube for collection in the bag. The bag may be attached to the patient's leg or bed depending upon the circumstances. The sheath may vary in size to improve fit, despite this the sheaths are usually too small or too large. Leakage and skin irritation are common problems. Keeping urine off the skin can prevent skin breakdown and irritation. Additionally, as application of the catheter is commonly performed by healthcare personnel, application can be difficult, cumbersome and awkward resulting in improper placement and function. For ambulatory patients, the leakage problems increase significantly.

Many efforts have been made at addressing these problems but none have proven successful or commercially viable. For example, a common approach has been to utilize a garment with an integral sheath. By elasticizing the garment, improved support and positioning may occur. However, application can become very difficult, particularly with bed-ridden patients. One example of such technology having a leg bag is shown in U.S. Pat. No. 4,957,487 issued to Gerow on Sep. 18, 1990, which is attached hereto.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present disclosure is directed to a male catheter assembly including a sheath portion with a proximal end and a distal end. The proximal end has a braided section for securing the sheath portion to a base of the penis shaft. The distal end has a connection portion for coupling to a leg bag and the like. The male catheter assembly may include a collection bag and a tube extending between the connection portion and the collection bag. Preferably, the sheath portion narrows from the proximal end towards the distal end.

In an aspect, the invention features an assembly including a proximal region including a sheath portion, the sheath portion including a braided section terminating in a proximal region opening adapted to encompass a male penis, a distal region including a connection portion, the connection portion terminating in a distal region opening to enable linking to one or more external devices, and a tube portion linking the proximal region to the distal region.

In another aspect, the invention features a method including providing an assembly, the assembly including a proximal region including a sheath portion, the sheath portion including a braided section terminating in a proximal region opening adapted to encompass a male penis, a distal region including a connection portion, the connection portion terminating in a distal region opening, and a tube portion linking the proximal region to the distal region, receiving the male penis in the proximal region opening, holding a base of the assembly at a base of the male penis, and pulling the sheath portion or tube portion distally to cause the braided section to fit snuggly around the male penis. The external catheter will not be able to tighten past a specific diameter therefore protecting the patient from any harm from accidental pulling of the device and preventing over tightening around the shaft of the penis.

In still another aspect, the invention features a male catheter assembly including a sheath portion including a proximal end and a distal end, the proximal end having a braided section for securing the sheath portion and the distal end having a connection portion. The device will have flexible rubber similar to internal Foley catheter and will be able to fit into a 'Stat lock' on the patient's leg that will secure the device from pulling. 'Stat locks' are widely used in the medical field to secure internal foley catheters from pulling, they have not been utilized in this way for an external catheter, hence another critical difference in this external catheter design.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The invention will be more fully understood by reference to the detailed description, in conjunction with the following figures, wherein.

DETAILED DESCRIPTION

Figure 1:
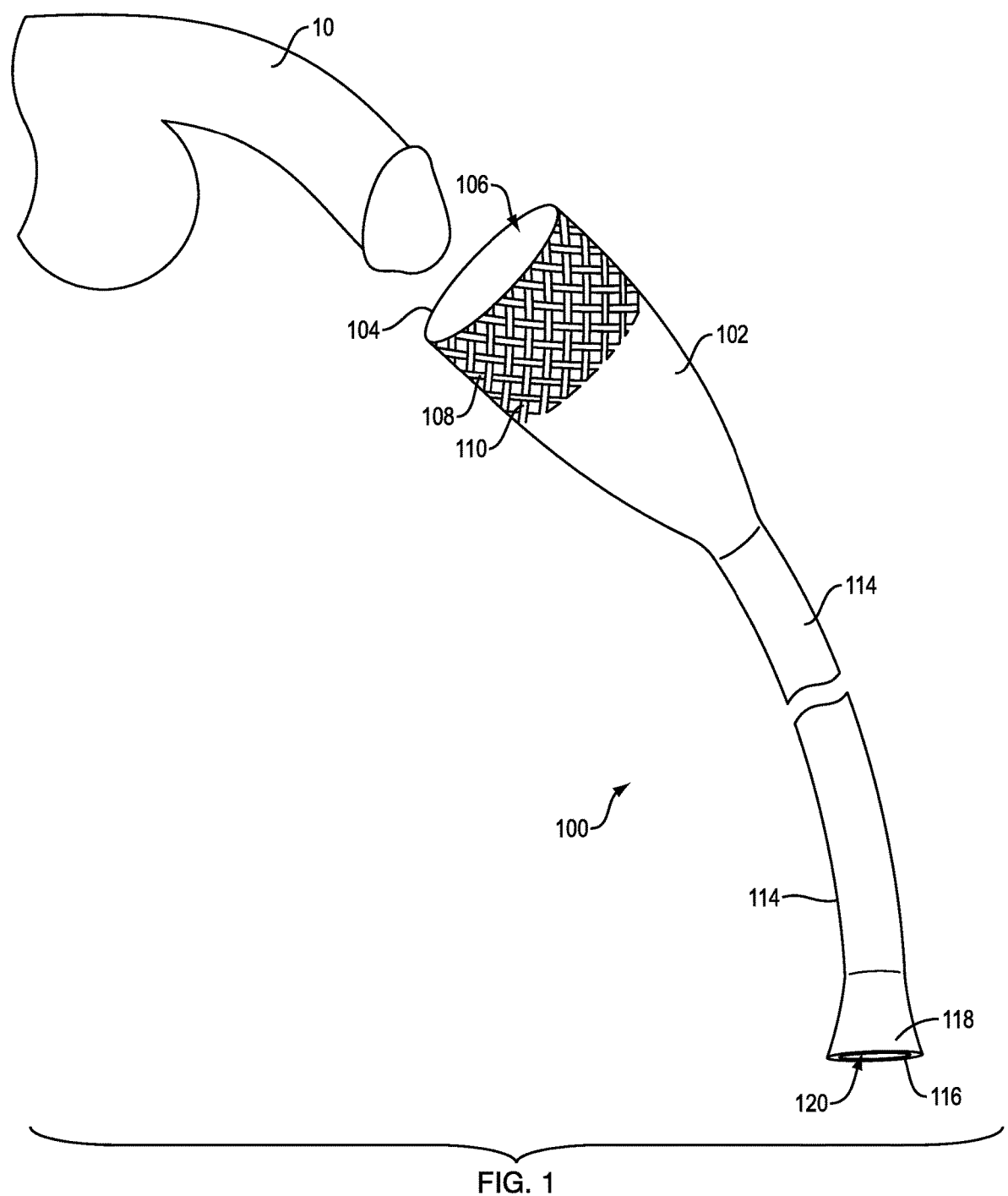
FIG. 1 is an exploded view of a male catheter assembly in accordance with the subject disclosure.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the term "or" is intended to mean an inclusive "or" rather than an exclusive "or." That is, unless specified otherwise, or clear from context, "X employs A or B" is intended to mean any of the natural inclusive permutations. That is, if X employs A, X employs B, or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Referring now to the FIG. 1, there is shown an exploded view of a male catheter assembly 100 to illustrate placement of the male catheter assembly 100 in accordance with the subject disclosure. The male catheter assembly 100 is easy to securely apply and allows the patient to be ambulatory or, if bed-ridden, urinate without being in a bathroom. Keeping the skin dry and without contact with urine which can cause skin breakdown and infection. The urine can be collected in a bag such as a leg bag or drainage bag or other container for subsequent disposal.

The male catheter assembly 100 includes a sheath portion 102 for enclosing a patient's penis 10. The sheath portion 102 has a proximal end 104 that forms an opening 106. The opening 106 is formed by a braided section 108. The braided section 108 may be integrally formed with the sheath portion 102. In the embodiment shown, the braided section 108 is separately formed and attached to the sheath portion 102 such as by hot melting, adhesive and/or the like. The braided section 108 may also be fabricated in one piece with medical grade silicone, surgical grade rubber, sterile nylon mesh and combinations thereof etc. The opening 106 varies in size for sealingly securing the sheath portion 102 to the penis. Typically, the male catheter assembly 100 is fabricated from silicone rubber, latex or other suitable material.

The braided section 108 is formed by a plurality of flat strips or strands 110 braided together to form a mechanism similar to the child's toy commonly known as Chinese finger cuffs or a finger trap toy. In one embodiment, the braided section 108 is formed from 4 strands woven as a bi-axial braid. In another embodiment, the braided section 108 has 16 woven strands. Preferably, the strands 110 are flat and relatively thinner the larger the number of strands. Spacing is formed between the strands 110 or the strands may overlap. The operation of the male catheter assembly 100 is described below with respect to FIGS. 2-4.

Still referring to FIG. 1, the male catheter assembly 100 narrows from the proximal end 104. A tube 114 extends from the sheath portion 102 to a distal end 116. The tube 114 is shown with break lines to indicate that the tube 114 may be configured of various lengths. In a leg bag application, the tube 114 would be a shorter length than in circumstances where the collection bag is attached to a patient's bed or wheelchair. Further, the tube 114 may include an occlusion device or clip (not shown) for selectively closing flow there through when changing and emptying the collection device.

The distal end 116 has a connection portion 118 adapted configured to connected to the collection device. The connection portion 118 may simply be a distal opening 120 for coupling to a hose barb, a Luer lock or other well known hose couplings now known and later developed. As such, a desired hose coupling mechanism may be inserted in the distal end 116. In FIG. 1, the connection portion is a universal connection.

Figure 2:
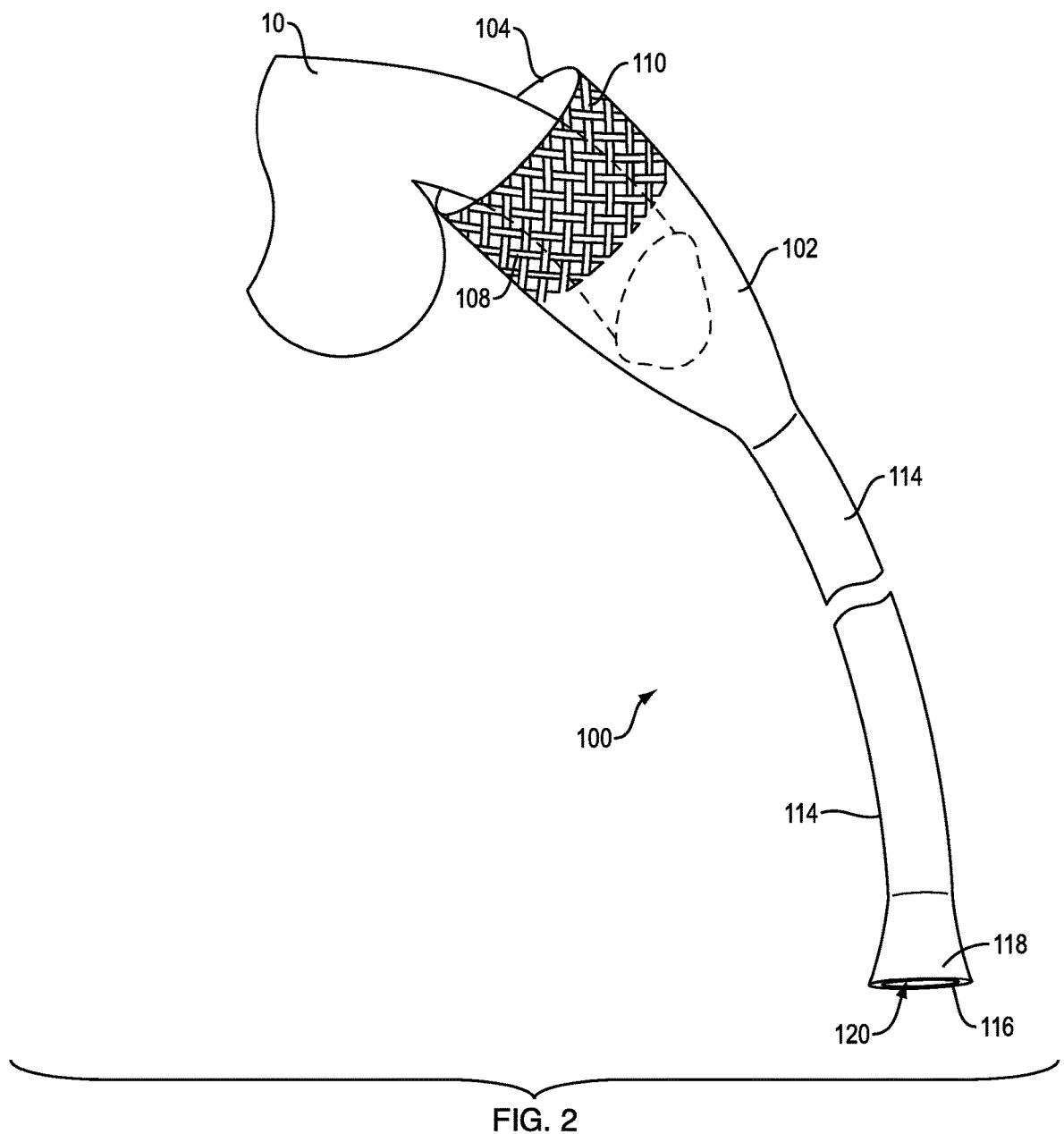
FIG. 2 illustrates the male catheter assembly being readied for placement in accordance with the subject disclosure.
Figure 3:
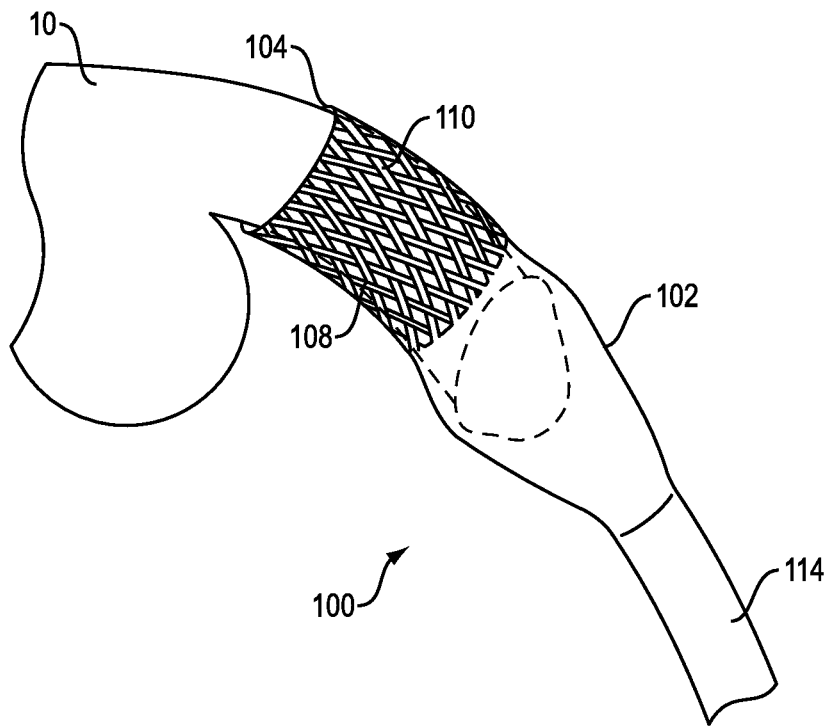
FIG. 3 illustrates the male catheter assembly secured in place in accordance with the subject disclosure.

Referring now to FIGS. 2 and 3, the male catheter assembly 100 being secured in place is shown. Initially, the male catheter assembly 100 is held in place with the penis 10 inserted through the proximal opening 106 (FIG. 2). By holding the proximal end 104 in place at the base of the penis shaft and gently pulling the sheath portion 102 or tube 114 distally, the spacing between the strands 110 closes to constrict the braided section 108. Once the braided section 108 constricts, the sheath portion 102 becomes secured to the shaft of the penis 10 (FIG. 3).

In the relaxed state, the proximal opening 106 is slightly larger than the penis shaft so that in the engaged state, the braided section 108 fits snugly around the shaft without need for adhesive. The male catheter assembly 100 can be made in a variety of sizes. The diameter of the proximal opening 106 and the length of the sheath portion 102 are two typical parameters to vary. The sheath portion 102 is also preferably fabricated from an elastic material to improve fit, retention and limit fluid flow in the proximal direction.

Figure 4:
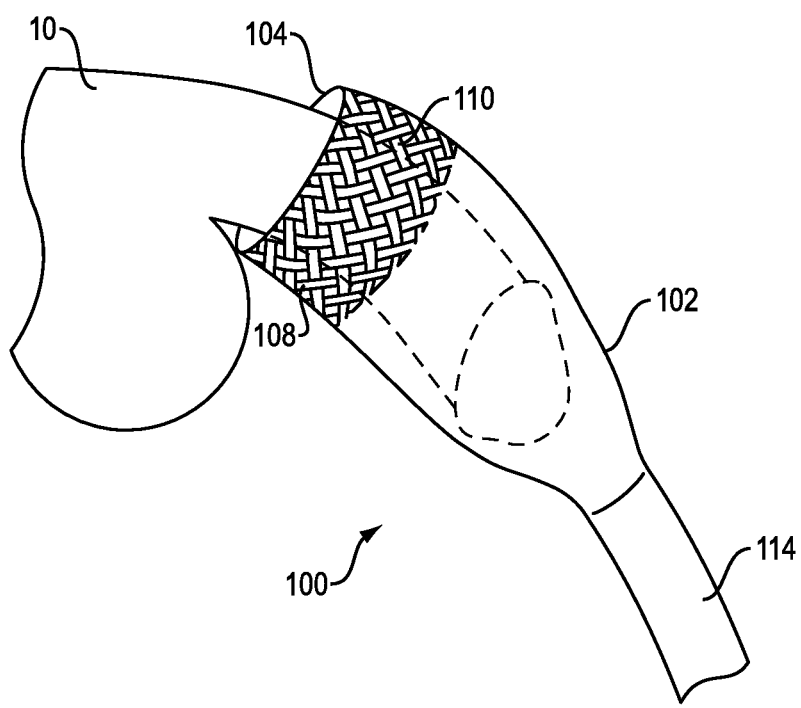
FIG. 4 illustrates the male catheter assembly being removed in accordance with the subject disclosure.

Referring now to FIG. 4, the male catheter assembly 100 may be easily removed by gently pulling the sheath portion 102 towards the body. This motion moves the braided section 108 back into the relaxed state. In the relaxed state, the proximal end 104 can be slid off for removal.

The male catheter assembly 100 may also include an adhesive band(s) located proximally or distally to the braided section. It will be appreciated by those of ordinary skill in the pertinent art that the functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., outlets, sheath portions, tubes, leg bags and the like) shown as distinct for purposes of illustration may be integrally formed and/or incorporated within other functional elements in a particular implementation.

The male catheter assembly 100 could also monitor strict 'I&Os' on male patients. Such monitoring is important for seeing how much a patient urinates, for example, if they were given a diuretic for congestive heart failure. It is also important for a male patient that may be incontinent to have accurate output measurements. It can be used during surgery in a sterile environment because the male catheter assembly 100 can be offered sterilized and in sterile packaging, but the male catheter assembly 100 does not need to be sterile for the medical units because the male catheter assembly 100 is an external catheter and will not be introducing bacteria into the body like the foley internal catheters can/do. Beneficially, the male catheter assembly 100 decreases Catheter-Associated Urinary Tract Infections (CAUTIs) in patients and offers a safe effective alternative to an internal catheter. CAUTIs cause urosepsis, the loss of patient lives and also cost the healthcare millions of dollars.

All patents, patent applications and other references disclosed herein are hereby expressly incorporated in their entireties by reference. While the subject technology has been described with respect to preferred embodiments, those skilled in the art will readily appreciate that various changes and/or modifications can be made to the subject technology without departing from the spirit or scope of the invention. For example, each claim may depend from any or all claims in a multiple dependent manner even though such has not been originally claimed.

What is claimed is:

1. An external male sheath catheter assembly, configured for use with a male patient, comprising:

(a) a sheath portion comprising: a proximal region; a tube region; and a distal region; wherein the tube region connects the proximal region to the distal region; and wherein the proximal region, the tube region, and the proximal region, are formed as a single sheath element;
(b) a braided section comprising at least four to 16 overlapping, spaced, and constrictible strands woven together as a biaxial braid; wherein the strands are flatter and thinner the greater the number of strands as compared to a fewer number of strands; wherein the braided section is configured to be integrally attached to an outer surface of the proximal region; and wherein the proximal region and the braided section are configured to provide a sealed attachment to a shaft and/or a base of the penis, after pulling proximally of the proximal region and/or the braided section over the penis, by then pulling on the sheath portion and/or the braided section in a distal direction, such that the spacing between the strands are reduced to constrict the braided section around both: (i) the proximal region; and (ii) the shaft and/or the base of the penis
(c) a flexible rubber drainage hose; wherein the distal region comprises a flared distal region opening comprising a hose coupling mechanism configured to be attached to a proximal end of the drainage hose; and
(d) a stat lock configured to attach the drainage hose to a leg of the male patient.

2. The assembly of claim 1 wherein the braided section is configured to be separately formed and then integrally attached to the outer surface of the proximal region.

3. The assembly of claim 2 wherein the braided section is integrally attached to the outer surface of the proximal region by hot melting.

4. The assembly of claim 2 wherein the braided section is integrally attached to the outer surface of the proximal region by an adhesive.

5. A method of using an external male sheath catheter assembly, the method comprising:
(A) providing the external male sheath catheter assembly of claim 1;
(B) pulling the proximal region and/or the braided section proximally over the penis;
(C) pulling distally on the sheath portion and/or the braided section in the distal direction to constrict the spacing between the strands to constrict the braided section around the proximal region and the shaft and/or the base of the penis to provide a sealed attachment to the shaft and/or the base of the penis;
(D) linking the flared distal region opening to an external urine collection bag via proximal and distal ends of the drainage hose via the hose coupling mechanism; and
(E) attaching a middle portion of the drainage hose to the stat lock.

6. The male catheter assembly as recited in claim 1 further comprising:
a collection bag; the drainage hose extending between the hose coupling mechanism and the collection bag.

7. The male catheter assembly as recited in claim 1 wherein a diameter of the sheath portion narrows from the proximal region towards the distal region.

8. The male catheter assembly as recited in claim 1 wherein the braided section comprises four strands integrally formed with the sheath portion.

9. The male catheter assembly as recited in claim 1 wherein the braided section comprises eight strands integrally formed with the sheath portion.

10. The male catheter assembly as recited in claim 1, wherein the strands of the braided section are made of nylon, surgical rubber, or a combination thereof.

11. A method for making an external male sheath catheter assembly, configured for use with a male patient, comprising the steps of:
(1) providing:
(a) a sheath portion comprising: a proximal region; a tube region; and a distal region;
(b) a braided section comprising at least four to 16 overlapping strands woven together as a biaxial braid; wherein the strands are flatter and thinner the greater the number of strands as compared to a fewer number of strands;
(c) a drainage hose; and
(d) a stat lock configured to attach the drainage hose to a leg of the male patient;
wherein the tube region connects the proximal region to the distal region;
wherein the proximal region, the tube region, and the proximal region are formed as a single sheath element;
wherein the distal region comprises a flared distal region opening comprising a hose coupling mechanism configured to be attached to a proximal end of the drainage hose;
wherein the braided section is configured to be integrally attached to an outer surface of the proximal region; and
wherein the proximal region and the braided section are configured to provide a sealed attachment to a shaft and/or a base of the penis, after pulling proximally of the proximal region and/or the braided section over the penis, by then pulling on the sheath portion and/or the braided section in a distal direction, such that the spacing between the strands are reduced to constrict the braided section around both: (i) the proximal region; and (ii) the shaft and/or the base of the penis; and
(2) providing a collection bag and the tube configured to extend between the connection portion and the collection bag.

12. The method of claim 11, wherein the braided section is separately formed and then slipped over and attached to the proximal region to become integrally attached to the proximal region.

13. The method of claim 11, wherein the braided section is integrally attached to the outer surface of the proximal region by hot melting.

14. The method of claim 11, wherein the braided section is integrally attached to the outer surface of the proximal region by an adhesive.

* * * * *